United States Patent [19]

Wall

[11] 4,372,314
[45] Feb. 8, 1983

[54] DENTAL SPONGE
[76] Inventor: W. Henry Wall, 2300 Henderson Mill Rd., Atlanta, Ga. 30345
[21] Appl. No.: 186,903
[22] Filed: Sep. 15, 1980
[51] Int. Cl.³ .............................................. A61F 13/00
[52] U.S. Cl. .................................... 128/296; 128/156; 433/136
[58] Field of Search ................................ 128/155–156, 128/285, 296, 292; 433/136, 137

[56] References Cited
U.S. PATENT DOCUMENTS

| | | | |
|---|---|---|---|
| 2,007,503 | 7/1935 | Riordan | 128/156 |
| 2,152,391 | 3/1939 | Spahn | 433/136 |
| 2,465,357 | 3/1949 | Correll | 128/296 |
| 2,884,925 | 5/1959 | Meynier, Jr. | 128/285 |
| 2,998,010 | 8/1961 | Griswold et al. | 128/285 |
| 3,216,422 | 11/1965 | Steiger et al. | 128/285 |
| 3,369,544 | 2/1968 | Crockford | 128/285 |
| 3,705,585 | 12/1972 | Saffro | 128/296 |
| 4,293,301 | 10/1981 | Mattsson | 433/136 |

OTHER PUBLICATIONS

*Surgery*, vol. 54, No. 4, Oct. 1963, p. 21, "Oxycel" advertisement.

*Primary Examiner*—C. Fred Rosenbaum
*Attorney, Agent, or Firm*—Jones & Askew

[57] ABSTRACT

A dental sponge constructed of absorbent material, which may include portions of oxidized cellulose or gelatin sponge material to be used as a hemostatic aid, for controlling bleeding following oral surgery or tooth extraction. The absorbent material is provided with an impervious non-absorbent coating covering a substantial portion of said absorbent material, with the coating defining an opening exposing the absorbent material through which fluid can flow. The sponge can be constructed in a number of shapes, and can be provided with projecting tab means used for handling the sponge.

3 Claims, 15 Drawing Figures

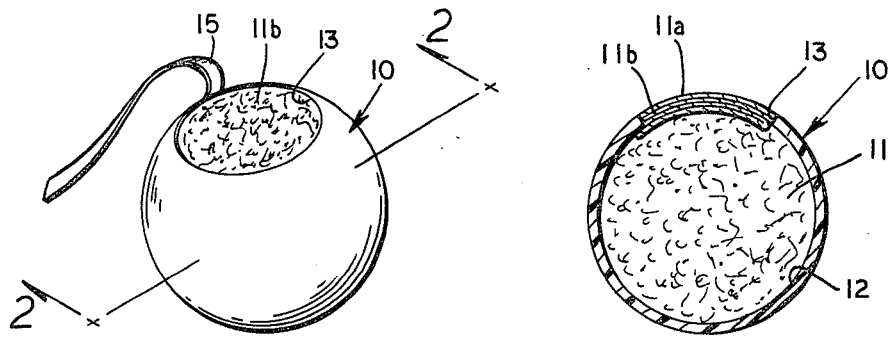
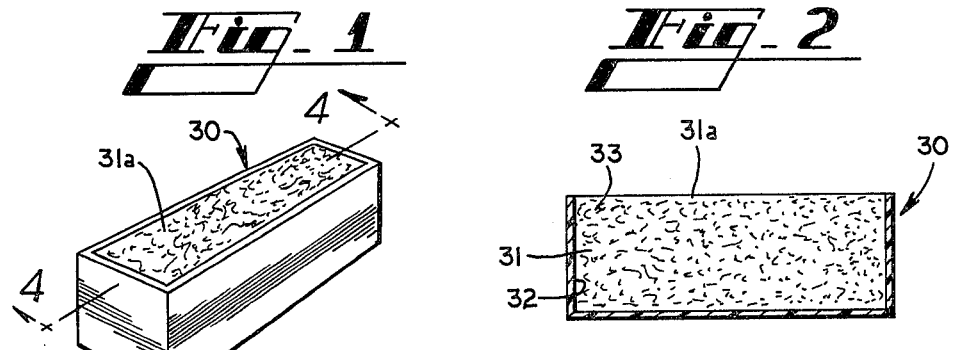
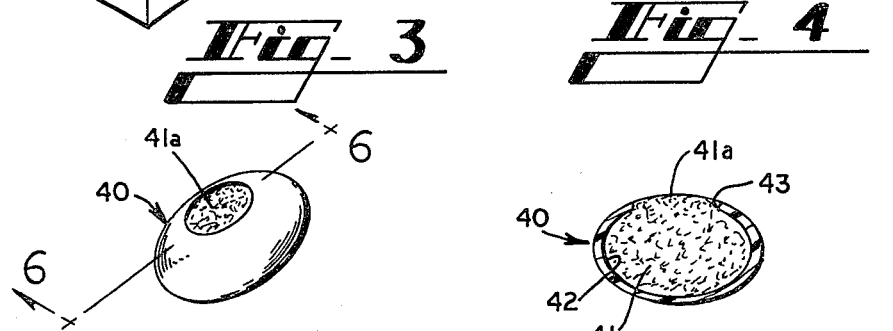
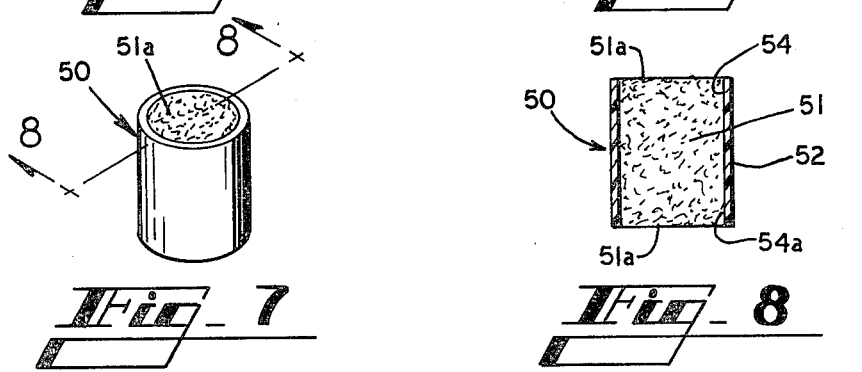

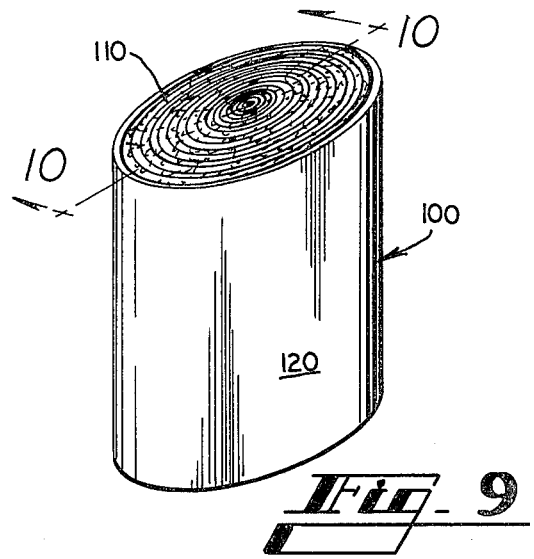
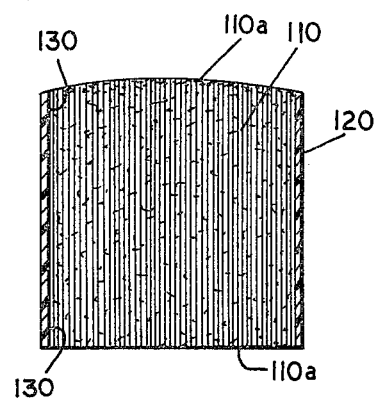
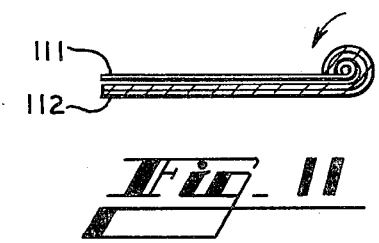
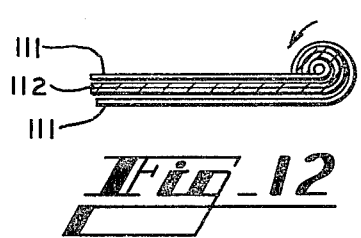
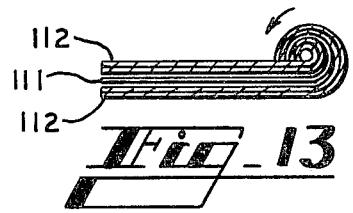
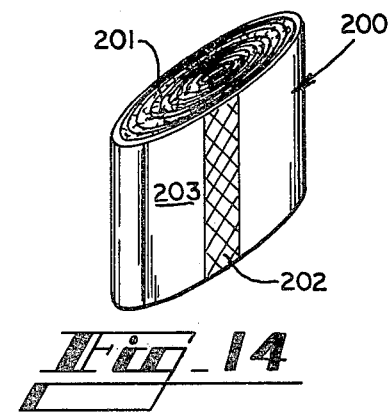
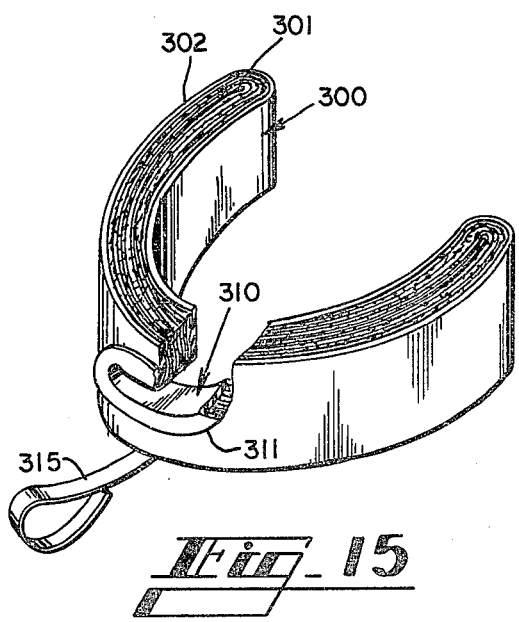

DENTAL SPONGE

TECHNICAL FIELD

This invention relates to an absorbent sponge and is more particularly concerned with a dental sponge for use in controlling bleeding.

BACKGROUND ART

Post-operative bleeding is a common surgical complication following oral surgery or tooth extraction. Further, certain patients have a history of prolonged bleeding or have a medical history leading the dentist to anticipate bleeding. Enzymes in the saliva in a patient's mouth tend to break down clots and therefore retard coagulation of the blood which is necessary to stop bleeding.

In a hemophillic patient, extra precaution is required to prevent complications which would require transfusions following tooth extraction or other forms of dental surgery.

A number of hemostatic agents, such as oxidized cellulose or gelatin sponge have been developed which will help in the control of post-operative bleeding. Oxidized cellulose, for example, is a styptic agent which forms a coating over the wound under which clotting occurs. However, none of the prior art hemostatic aids provides any means for holding the saliva away from open wounds.

SUMMARY OF THE INVENTION

The above indicated disadvantages have been overcome by the dental sponge of the present invention which, generally described, includes the coating or encasing of a major portion of an absorbent dental sponge with impervious non-absorbent material to hold saliva in a patient's mouth away from an open wound to promote quick coagulation of the blood to control post-operative bleeding. The dental sponge of the present invention preferably includes the use of predetermined portions of a hemostatic agent in the absorbent material of the improved dental sponge. The construction of the absorbent material preferably comprises alternating layers of gauze and non-woven material.

Another feature of the present invention includes the provision of a projecting tab for use in handling the dental sponge.

A further feature of the present invention includes providing particular shapes of the dental sponge to provide optimum bleeding control following various types of operative procedures.

Thus, it is an object of the present invention to provide an improved dental sponge for use in controlling post-operative bleeding which is simple in construction and use, economical to manufacture and reliable in performance.

Another object of the present invention is to provide an improved dental sponge constructed and shaped to promote coagulation of blood at operative sites while isolating such sites from saliva in the mouth.

Another object of the present invention is to provide an improved dental sponge having a novel construction of absorbent material.

These and other objects and advantages of the invention will become apparent after reading the following description of the illustrative embodiments, with reference to the attached drawing wherein like reference numerals have been used to refer to like parts in the several Figures.

BRIEF DESCRIPTION OF THE DRAWINGS

FIG. 1 is a perspective view of a dental sponge embodying the principles of the present invention.

FIG. 2 is a vertical cross-sectional view taken along line 2—2 of FIG. 1.

FIG. 3 is a perspective view of a second embodiment of the dental sponge of the present invention.

FIG. 4 is a vertical cross-sectional view taken along line 4—4 of FIG. 3.

FIG. 5 is a perspective view of a third embodiment of the dental sponge of the invention.

FIG. 6 is a vertical cross-sectional view taken along 6—6 of FIG. 5.

FIG. 7 is a perspective view of a fourth embodiment of the dental sponge of the invention.

FIG. 8 is a vertical cross-sectional view taken along line 8—8 of FIG. 7.

FIG. 9 is a perspective view of a fifth embodiment of the dental sponge of the invention.

FIG. 10 is a vertical cross-sectional view taken along line 10—10 of FIG. 9.

FIGS. 11–13 show diagrammatically various method for rolling absorbent material to form a layered construction for use in a dental sponge embodying the present invention.

FIG. 14 is a perspective view of a sixth embodiment of the dental sponge of the invention.

FIG. 15 is a perspective view of a seventh embodiment of the dental sponge of the invention, for use following a complete mouth of teeth extraction; with a portion broken away to show interior detail.

DESCRIPTION OF THE ILLUSTRATIVE EMBODIMENTS

Referring to the drawings in which like numerals represent like parts throughout the several views, a dental sponge embodying the principles of the present invention is shown in FIG. 1 and generally represented by reference numeral 10. Dental sponge 10 is spherical in shape and includes absorbent material 11, such as gauze or cotton, within an impervious coating 12 covering a major portion of the absorbent material. The absorbent material may include predetermined portions 11b of a hemostatic aid, such as oxidized cellulose or a gelatin sponge.

The impervious coating 12 defines a circular fluid passageway opening 13 through which a slight portion 11a of the absorbent material projects and through which fluid can flow into the body of the absorbent material contained within coating 12. The hemostatic material can advantageously be located at the opening 13, as shown in FIG. 2. The dental sponge 10 is provided with a projecting tab 15 which can be used in handling the sponge.

FIGS. 3 and 4 show a second embodiment of the dental sponge 30 which is rectangular in shape and includes a body of absorbent material 31 having an impervious non-absorbent coating 32 which defines an opening 33 through which the absorbent material at 31a is exposed.

A third embodiment of the dental sponge is shown in FIGS. 5 and 6 and generally represented by reference number 40. Sponge 40 is elliptical in shape and includes a body of absorbent material 41 having an impervious non-absorbent coating 42. An absorbent material exposure opening 43 is formed in the long dimension of the elliptical shape through which a slight amount of the material 41a projects and through which fluid can flow into the interior of the elliptical coating 42.

A fourth embodiment 50 of the dental sponge is shown in FIGS. 7 and 8 and is cylindrical in shape and includes an absorbent body portion 51 having an impervious non-absorbent coating 52 extending around the circumference of body 51 with the axial ends open to define a pair of openings 54, 54a for providing passageways for fluid flow into the absorbent body and through which slight portions 51a of the absorbent material project.

A fifth embodiment of the present invention is shown in FIGS. 9 and 10, and includes a preferred construction of the absorbent material that can be used with any of the embodiments disclosed herein. A dental sponge 100 includes a cylinder of absorbent material 110 comprising alternating layers of a woven material 111, such as gauze, and a non-woven material 112, such as cotton. The layers are built up by rolling sheets of woven material 111 and non-woven material 112 together as shown in FIGS. 11-13. In FIG. 11 one sheet of each material is layed next to the other and rolled. In FIG. 12, a sheet of non-woven material 112 is sandwiched between two sheets of woven material 111 and the combination is rolled together. FIG. 13 shows a similar rolling of a sheet of woven material 111 between two sheets of non-woven material 112. Although rolling or folding of superimposed sheets is often the most convenient manner in which to form the layered construction shown, any manner of building up the layers of woven and non-woven materials is within the concept of the invention.

An advantage of utilizing the layered construction as described above is ease of manufacture, since the layers can be spun together on a mandrel. It is also believed that the rolled or folded construction promotes greater capillary action in the fibers of the absorbent material by lining up the fibers with cut ends at the fluid passageway openings, thereby increasing the rate of absorption of blood. Rolling or folding also allows the compressibility of the dental sponge to be controlled. For example, a tightly rolled sponge would not be subject to excessive compression caused by the patient biting down on the sponge.

When oxidized cellulose or another hemostatic agent is used in a sponge having a rolled or folded construction, one or more layers of oxidized cellulose (not shown) are preferably rolled or folded with the layers of woven and non-woven absorbent material. An optimum proportion of oxidized cellulose in any of the embodiments described herein for promoting coagulation is 15–20% of the absorbent material in the sponge.

The dental sponge 100 also includes a film of impervious material 120 wrapped around the absorbent material to form a cylindrical sponge with exposed portions 110a of the absorbent material projecting slightly from openings 130 for contacting a wound in the mouth.

A sixth embodiment of the invention is shown as dental sponge 200 in FIG. 14. A core of absorbent material 201 is formed by folding layers of woven and non-woven material to form the shape of a cylinder having an elliptical cross-section. A film of plastic impervious material 203 is wrapped around the absorbent material 201 and heat sealed to form a joint 202.

A seventh embodiment of the invention is shown as dental sponge 300 in FIG. 15. The dental sponge 300 is formed from elongate layers of absorbent material 301 shaped in a semi-circular manner to completely cover both the upper and lower gums following extraction of all of the patient's teeth. The upper and lower surfaces of the sponge 300 are open to contact the wound, and the side surfaces are covered with an impervious material 302. An air passage channel 310 is provided transversely through to impervious cover 302 and absorbent material 301 at the center of the semi-circular sponge 300. The channel 310, shown partially broken away in FIG. 15, allows the patient to breathe while biting on the sponge 300. The channel 310 can also be used to accomodate a suction line while continuing to permit breathing. The channel 310 is preferably constructed of stiff plastic to prevent the channel from being closed off under pressure of the patient's jaws. An annular flange 311 is attached to each end of the channel 310 to hold the channel in place within the sponge 300. This eliminates any danger of the channel becoming displaced and swallowed by the patient, and also provides a stiffer construction for the channel 310. A loop 315 is attached to the impervious cover 302. The loop 315 can be grasped to assist in inserting, positioning, and removing the dental sponge 300.

The impervious coating in each of the above embodiments can be formed, for example, of a number of suitable plastic materials which can be applied to the surface of the absorbent material either by spraying or dipping the absorbent body. Alternatively, preformed impervious covers could be formed with the desired openings and the absorbent material could be inserted in the covers. In the case of open-ended sponges, such as shown in FIGS. 7, 9, and 14, a length of impervious material of width approximately equal to the height of the sponge can be wrapped around the absorbent material and joined at overlapping edges of the impervious material. The joint can be heat sealed if plastic is ued as the impervious material. A heat sealed joint 202 is shown in FIG. 14.

A handling tab such as the tab 15 of FIG. 1 can be provided in each of the embodiments and is preferably bonded to or integrally formed with the coating or cover.

The material from which the impervious coating and tabs is made should be soft and flexible enough so as not to irritate the patient's mouth, and must not be porous to liquids. Polyethylene and polyvinylchloride are suitable materials, but the invention is not limited thereto. The impervious coating may be a thin film of material, much thinner than as illustrated in the drawing.

In use of the dental sponges shown in the above-described embodiments of the invention, the particular sponge is positioned in the patient's mouth with the fluid passageway opening or openings over the open wound. The blood oozing from the wound is absorbed by the absorbent material into the interior of the sponge. The sponge should be placed over the socket left by an extraction rather than down into the socket, so that a clot will form over the full height and depth of the socket. The impervious coating or covering prevents saliva from contacting the blood and retains the blood within the sponge. The patient therefore experiences less taste of blood and can swallow more easily. If the absorbent material includes a hemostatic agent as described above, the agent will promote coagulation of the blood.

For example, the first, and third embodiments shown in FIGS. 1 and 5, respectively, are shaped for use primarily on a wound left by the extraction of a single tooth. After placement of the sponge, the patient can bite gently on the sponge to hold it in place until the bleeding stops. The second embodiment of FIG. 3 is shaped for use on adjacent wounds left by the extraction of two adjacent teeth.

The fourth, fifth and sixth embodiments shown in FIGS. 7, 9 and 14, are open at opposite ends of the sponge and therefore can be used either for a wound on only one jaw or for opposite wounds on the upper and lower jaws. The somewhat elongate shape of the sponge 200 of the sixth embodiment makes it useful for multiple adjacent extractions. The seventh embodiment of FIG. 15 is useful for extractions of all the teeth from one jaw or all the teeth from both jaws, as described above. If tabs such as tab 15 of FIG. 1 and loop 315 of FIG. 15 are attached to the sponge, the tab is used to assist in maneuvering the sponge inside the patient's mouth. Of course, use of dental sponges embodying the invention is not limited to teeth extractions, but can be used to control bleeding following all types of oral surgery.

It should now be apparent that the above described illustrative embodiments of the applicant's improved dental sponge are capable of obtaining the above stated objects and advantages. That those skilled in the art may make modifications in the details of construction without departing from the spirit of the invention which is to be limited only by the scope of the appended claims.

I claim:

1. A dental sponge for controlling bleeding from a wound in the mouth and preventing saliva from contacting said wound comprising a cylindrical absorbent member including a hemostatic agent, and a saliva-resistant plastic film encircling the cylindrical surface of said absorbent member, said absorbent member being exposed at its ends.

2. The dental sponge of claim 1, wherein said hemostatic agent is a material selected from the group consisting of oxidized cellulose and gelatin sponge.

3. The dental sponge of claim 1, wherein said absorbent material comprises a mixture of cotton and between 15–20% oxidized cellulose.

* * * * *